(12) United States Patent
Bardagjy et al.

(10) Patent No.: US 10,312,656 B1
(45) Date of Patent: Jun. 4, 2019

(54) WAVELENGTH TUNING FOR DIFFRACTIVE OPTICAL ELEMENTS OF STRUCTURED LIGHT PROJECTORS

(71) Applicant: Facebook Technologies, LLC, Menlo Park, CA (US)

(72) Inventors: Andrew Matthew Bardagjy, Fremont, CA (US); Joseph Duggan, San Francisco, CA (US); Cina Hazegh, Walnut Creek, CA (US); Fei Liu, San Jose, CA (US); Mark Timothy Sullivan, Mountain View, CA (US); Simon Morris Shand Weiss, Redwood City, CA (US)

(73) Assignee: Facebook Technologies, LLC, Menlo Park, CA (US)

( * ) Notice: Subject to any disclaimer, the term of this patent is extended or adjusted under 35 U.S.C. 154(b) by 210 days.

(21) Appl. No.: 15/623,633

(22) Filed: Jun. 15, 2017

(51) Int. Cl.

| | |
|---|---|
| *A61B 5/00* | (2006.01) |
| *G01B 9/02* | (2006.01) |
| *G01J 3/10* | (2006.01) |
| *G01J 3/18* | (2006.01) |
| *G02B 5/18* | (2006.01) |
| *G02F 1/33* | (2006.01) |
| *G03F 7/20* | (2006.01) |
| *H01S 3/08* | (2006.01) |

(Continued)

(52) U.S. Cl.
CPC ........ *H01S 3/08009* (2013.01); *A61B 5/0059* (2013.01); *G01B 9/02091* (2013.01); *G01J 3/10* (2013.01); *G01J 3/1838* (2013.01); *G01N 21/4795* (2013.01); *G02B 5/1866* (2013.01); *G02F 1/33* (2013.01); *G03F 7/2024* (2013.01); *G06T 7/521* (2017.01)

(58) Field of Classification Search
CPC ............ H01S 3/08009; G01N 21/4795; G01B 9/02091; G01J 3/10; G01J 3/1838; A61B 5/0059; G02B 5/1866; G02B 27/44; G03F 7/2024; G02F 1/33; G06T 7/521
See application file for complete search history.

(56) References Cited

U.S. PATENT DOCUMENTS

| | | | |
|---|---|---|---|
| 2007/0040997 A1* | 2/2007 | Yamauchi | ............. G02B 27/46 353/97 |
| 2009/0185274 A1* | 7/2009 | Shpunt | ............... G02B 27/0944 359/558 |

(Continued)

*Primary Examiner* — Kimberly N. Kakalec
(74) *Attorney, Agent, or Firm* — Fenwick & West LLP (57) ABSTRACT

A wavelength tuning system determines a temperature calibrated to a DOE of a structured light (SL) projector. The wavelength tuning system includes a camera and controller. The camera captures images of a SL pattern projected by the SL projector. The controller generates tuning instruction. The tuning instructions cause a wavelength regulator of the SL projector to set a light source of the SL projector to different temperatures. The tuning instruction also cause the camera to capture images of the structured light pattern at each of the different temperatures. Using at least some of the captured images, the controller determines the temperature calibrated to the DOE. In one embodiment, the temperature calibrated to the DOE corresponds to a wavelength of light emitted by the light source that result in an estimated minimum power of a zeroth order diffracted beam of the SL pattern.

20 Claims, 4 Drawing Sheets

(51) Int. Cl.
    *G01N 21/47*         (2006.01)
    *G06T 7/521*         (2017.01)

(56) References Cited

U.S. PATENT DOCUMENTS

2011/0188054 A1*   8/2011   Petronius ................ B23P 11/00
                                                                356/610
2012/0281240 A1*  11/2012   Cohen .................. G06K 9/2036
                                                                356/610
2018/0061034 A1*   3/2018   Zhao .................. G02B 27/0172

* cited by examiner

WAVELENGTH TUNING FOR DIFFRACTIVE OPTICAL ELEMENTS OF STRUCTURED LIGHT PROJECTORS

BACKGROUND

The present disclosure generally relates to wavelength tuning, and specifically to wavelength tuning for a structured light projector including one or more diffractive optical elements (DOE).

Structured light projectors are used for depth measurement in head-mounted display (HMD) systems, such as systems used in virtual reality and augmented reality applications. A structured light projector is typically composed of a light source that emits light and a DOE that uses the emitted light to generate a structured light pattern. Performance of DOEs is highly dependent on wavelength, and inconsistencies in manufacturing DOEs and/or light sources may cause an optimal wavelength of DOEs to vary from its design wavelength (i.e., wavelength it is designed to operate at), even between DOEs from the same lot. Examples of inconsistency in manufacturing include incorrect etch depth in e.g., lithographic processes, material shrinkage in compression molding, or incomplete material flow in injection/compression molding applications (e.g., due to trapped gas). Any different in feature period and feature height of a DOE can cause change in its design wavelength. Existing wavelength tuning methods for a structured light projector determine wavelengths calibrated to the light source (e.g., to produce maximum optical power). However, those exiting systems fail to produce optimal structured light patterns because variation in the optimal wavelength can result in a system where light emitted from the source is at different wavelength than the optimal wavelength for the associated DOE.

SUMMARY

A wavelength tuning system tunes a wavelength of an illumination source of a structured light projector to optimize one or more structured light patterns produced by the DOE. The DOE generates one or more structured light patterns using light emitted from a light source of the structured light projector. For example, the wavelength tuning system determines a temperature calibrated to the DOE. The temperature calibrated to the DOE corresponds to a wavelength of light emitted by a light source of the structured light projector that results in at least one performance metrics meeting a corresponding threshold.

The wavelength tuning system includes a controller and a camera assembly. The controller generates tuning instructions. The tuning instructions control a wavelength regulator of the structured light projector, and can cause the wavelength regulator to set the light source to different temperatures. In one embodiment, the wavelength regulator is a thermal electrical cooler that is coupled directly or in some case integrated into the light source. In an alternative embodiment, the wavelength regulator is a resistive heater. In some embodiments, the wavelength regulator is included in a mount on which the structured light projector is attached. The tuning instructions control the camera assembly, and can cause the camera assembly to capture images of the structured light pattern generated by the DOE at each of the different temperatures over, e.g., a set of temperatures. The camera assembly captures, in accordance with the tuning instructions, images of the structured light pattern projected by the structured light projector.

Using one or more of the captured images, the controller determines the temperature calibrated to the DOE. In one embodiment, the temperature calibrated to the DOE corresponds to a wavelength of light emitted by the light source that result in an estimated minimum power to a zeroth diffracted beam of the structured light pattern.

The figures depict embodiments of the present disclosure for purposes of illustration only. One skilled in the art will readily recognize from the following description that alternative embodiments of the structures and methods illustrated herein may be employed without departing from the principles, or benefits touted, of the disclosure described herein.

DETAILED DESCRIPTION

Figure 1:
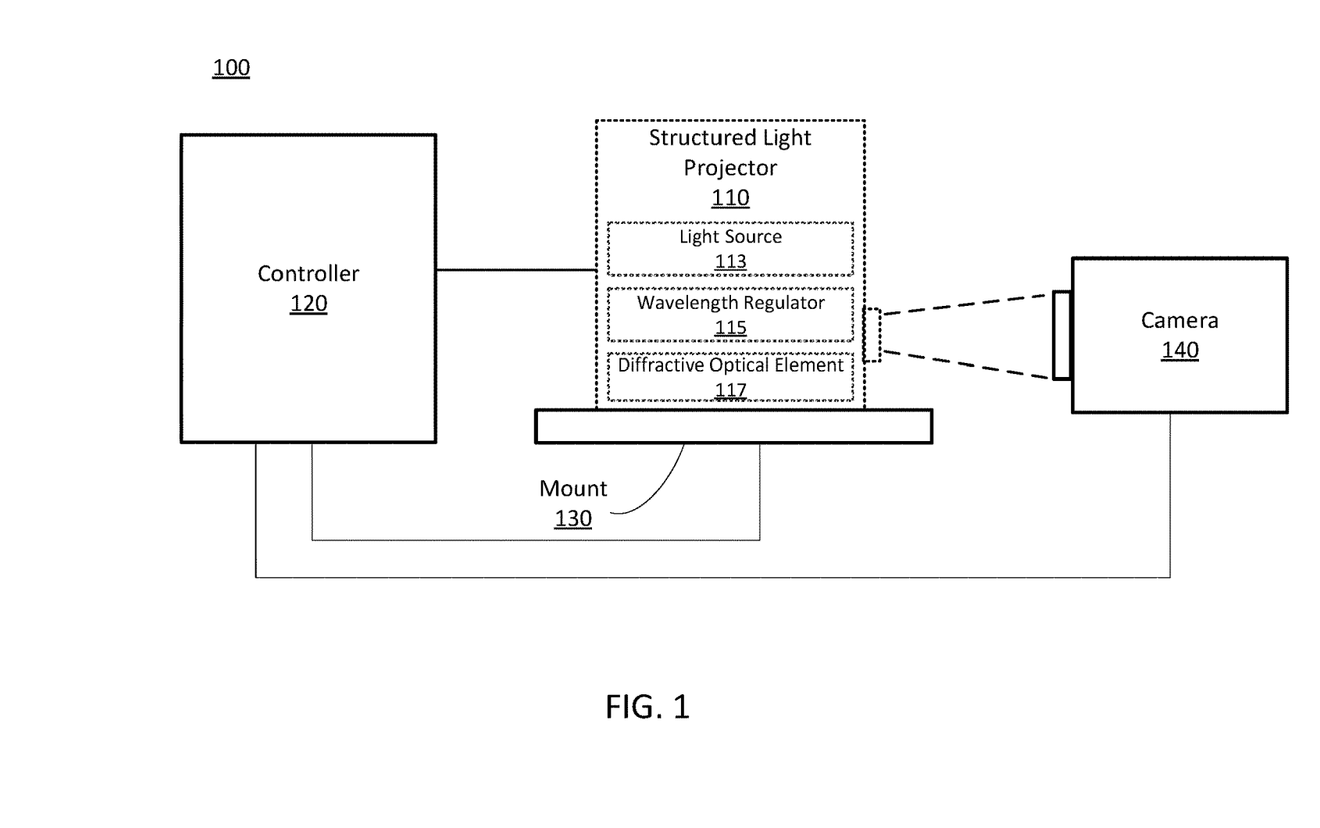
FIG. 1 is a diagram of a wavelength tuning system, in accordance with an embodiment.

FIG. 1 is a diagram of a wavelength tuning system 100, in accordance with an embodiment. The wavelength tuning system 100 is configured to determine a temperature that is calibrated to a DOE 117 of a structured light projector 110. The wavelength tuning system 100 of the embodiment of FIG. 1 includes a controller 120, a mount 130, and a camera assembly 140. In other embodiments, the wavelength tuning system 100 can have additional or different components.

The structured light projector 110 generates a structured light pattern in accordance with tuning instructions provided by the controller 120. The structured light projector 110 includes a light source 113, a wavelength regulator 115, and the DOE 117. The structured light projector 110 may include additional or different components. For example, the structured light projector 110 can have more than one DOE 117, and each DOE 117 may have different configuration and generates different types of structured light pattern. As another example, the wavelength regulator may be included in the mount 130, instead of the structured light projector 110. Also, the structured light projector 110 may have more than one light source 113, and each light source 113 emits light at a different wavelength.

In the embodiment of FIG. 1, the light source 113 is a laser light source. The light source may emit light in a visible band, an infrared band, some other optical band, or some combination thereof. The light source may include, e.g., a laser diode, a laser, a tunable laser, or some other source that generates light having properties that enable the DOE 117 to generate a structured light pattern. A wavelength of light emitted by the light source 113 varies with temperature. A different temperature of the light source 113 corresponds to a different wavelength of the emitted light. For example, the wavelength of the emitted light increases, e.g., approximately linearly, as the temperature of the light source 113 increases. In alternative embodiments, the light source 113 can be other types of light sources than laser light source, such as vertical-cavity surface-emitting laser (VCSEL), Fabry-Perot (FP) laser, distributed feedback (DFB) laser, light emitting diode (LED), etc.

The wavelength regulator 115 regulates wavelength emitted from the light source 113 by adjusting temperatures of the light source 113, in accordance with tuning instructions generated by the controller 120. A different temperature of the light source 113 corresponds to a different wavelength of light emitted by the light source 113. In one embodiment, the wavelength regulator 115 is a thermal electric cooler. For example, the wavelength regulator 115 includes a hot side, a cold side, and an array of alternating n- and p-type semiconductor elements between the two sides. The hot side and cold side each includes an electrical conductor that is coupled to an electrical voltage supplier. The electrical voltage supplies provides an electrical voltage across the two sides and crease an electrical current. Cooling occurs when the current passes through one or more pairs of semiconductor elements from n-type to p-type. Heating occurs when the current passes from p-type to n-type. The wavelength regulator 115 is coupled directly to the light source 113, so that temperature of the light sources changes with the cooling or heating of the wavelength regulator 115. The wavelength regulator 115 may have more than one thermal electric cooler. For example, two or more thermal electrical coolers are connected in parallel. The cooling/heating ability of the wavelength regulator 115 is proportional to the number of thermal electric coolers in it. The wavelength regulator 115 can also be a resistive heater. In the resistive heater, heat is generated based on passage of an electric current through a conductor.

In an alternative embodiment, the wavelength regulator 115 adjusts wavelength of light emitted from the light source 113 by adjusting a drive current that is supplied to the light source 113. For example, wavelength of the emitted light increases when the wavelength regulator 115 increases the drive current supplied to the light source 113.

The DOE 117 generates structured light patterns using light emitted from the light source 113. The DOE 117 can generate one-dimensional or two-dimensional beam array. Example structured light patterns include: dot matrix pattern, single line pattern, sinusoid pattern, multi (spatial) tone pattern, checkerboard pattern, start pattern, diffuse light, and grid pattern. The DOE 117 is a diffraction grating. For example, the DOE 117 is a light diffuser that generates diffuse light. In one embodiment, the diffraction grating has a repetitive pattern etched on a surface of a substrate. The repetitive pattern of the diffraction grating allows the diffraction grating to diffract an input beam (e.g., light emitted by the light source 113) into several beams travelling in different directions. The diffracted beams have different orders. The diffracted beam in the direction of the input beam is the zeroth order diffracted beam, which is the un-diffracted continuation of the input beam. There are diffracted orders on both sides of the zeroth order beam. For example, the diffracted beams adjacent to the zeroth order diffracted beam are the first order diffracted beam. As getting further from the zeroth order diffracted beam, diffracted beams have higher orders.

In some embodiments, it is preferred that the zeroth order diffracted beam has a minimum power, which indicates that the DOE 117 has a higher diffraction efficiency for one or more non-zero order beams and a low diffraction efficiency for the zero order beam. In one embodiment, a diffraction efficiency of the DOE 117 is determined by a ratio of the power of the zeroth order diffracted beam to power of light incident on the DOE 117. Diffraction efficiency of the diffracting grating varies with wavelength of the input beam. The diffraction grating has an optimal wavelength at which the diffraction grating has the lowest diffraction efficiency for the zero-order beam—i.e., maximum power is being provided to the higher order diffracted beams. For a wavelength lower or higher than the optimal wavelength, power is redirected from one or more of the higher order beams to the zero-order beam, thus reducing the effectiveness of the structured light pattern.

The mount 130 holds the structured light projector 110. The mount 130 couples the structured light project 110 to a mounting area via a coupling assembly. The coupling assembly holds the structured light projector 110 to the mounting area. The coupling assembly may include, e.g., tabs, screws, mechanical arms, some other assembly that is configured to hold a structured light projector 110 in position, or some combination thereof. In some embodiments, the structured light projector 110 held by the mount 130 is fixed in place at the mounting area. In alternate embodiments, the mount 130 may be configured to adjust a position and/or orientation of the structured light projector 110 by one degree of freedom two degrees of freedom, three degrees of freedom, four degrees of freedom, five degrees of freedom, or six degrees of freedom in accordance with imaging instructions (provided by the controller 120). For example, the mounting area may be affixed to a mechanical stage that has up to six degrees of freedom. The mount 130 may also provide electrical power to the structured light projector 110 during a wavelength tuning process.

In some embodiments, the structured light projector 110 is part of some other device (e.g., a HMD, a console, etc.). In these cases, the mount 130 may couple to the device that incorporates the structured light projector 110.

The camera assembly 140 captures images of a structured light pattern projected by the structured light projector 110. The camera assembly 140 includes one or more cameras. In some embodiments, the camera assembly 140 may also include a positioning stage. A camera may be, e.g., an array (1D or 2D) of photodiodes, a charge coupled display (CCD) array, some other device capable of detecting some or all of the structured light pattern, or some combination thereof. The camera captures the images in accordance with tuning instructions generated by the controller 120. For example, the camera collects structured light emitted from structured light projector 110, converts the collected structured light into digital signals, and generate the images based on the digital signals. The captured images include images of the structured light pattern captured at different temperatures values of the light source 113 (i.e., different wavelengths). For example, the camera captures one or more images of the structured light pattern at each temperature of the light source 113.

The controller 120 generates the tuning instructions. The tuning instructions cause the wavelength regulator 115 to set the light source 113 (e.g., an IR laser diode) to different temperatures of a set of temperatures. The controller 120 determines a range of temperatures. The temperature range corresponds to an expected range of variation in optical wavelengths for different DOEs 117. Different DOEs 117 can have different optimal wavelengths even though they have a same design wavelength (i.e., the wavelength the DOEs 117 are designed to operate at). This can be due to, for example, inconsistency in manufacturing. Examples of inconsistency in manufacturing include incorrect etch depth in e.g., lithographic processes, material shrinkage in compression molding, or incomplete material flow in injection/compression molding applications (e.g., due to trapped gas). In some embodiments, the expected range of variation in optical wavelengths is determined experimentally using some sample set of DOEs 117 (e.g., 100 DOEs) that are designed to have a particular optimal wavelength (but which in practice actually can have optimal wavelengths that are different from the design optimal wavelength). For example, optimal wavelengths of each of the sample set of different DOEs are determined to obtain a distribution of optimal wavelengths, e.g., the design optimal wavelength plus and minus 10 nm. As noted before, there is a relationship between temperature and wavelength for the laser source, for example, with 1° C. increase in temperature, wavelength may increase by 0.3 nm. In some embodiments, the temperature range lower boundary and upper boundary correspond to wavelength values of the distribution (e.g., ±three standard deviations of the distribution of optimal wavelengths). In one embodiment, the temperature range is 40 to 60° C. which correspond to 852 nm to 848 nm. In alternate embodiment, a user of the wavelength tuning system 100 may provide the controller 120 with temperature values that set the range of temperatures.

The controller 120 may also determine an increment between different temperatures in the set of temperatures. The increment between adjacent temperature values in the set of temperatures ("temperature increment") can be constant. For example, the controller 120 determines that the temperature increment is 0.2° C. In one embodiment, the increment is arbitrary (e.g., 0.01 nm). In an alternative embodiment, the increment is determined based on sensitivity of diffraction efficiency of the DOE 117 to change in wavelength. For example, if the diffraction efficiency of the DOE 117 changes significantly with wavelength, it is preferred to have a relatively small temperature increment. Similarly, if the diffraction efficiency is less sensitive to change in wavelength, the temperature increment can be larger.

The temperature increment can also be variable. In one embodiment, the controller 120 determines that an increment for temperatures close to a mid-temperature that corresponds to a mean (or median) value of the distribution of optimal wavelengths that is smaller than an increment for temperatures further from the mid-temperature. For example, the set of temperatures is in a range from 40 to 60° C., where the mid-temperature is 50° C. The increment between 45 and 55° C. is 0.5° C., while the increment in the range from 40 to 45° C. and in the range from 55 to 60° C. is larger, e.g., 1° C.

In some embodiments, the controller 120 does not determine an increment. The controller 120 instructs the wavelength regulator 115 to increase temperature of the light source 113 from an initial/lower temperature (e.g., 40° C.) to a final/higher temperature (e.g., 60° C.). Because temperature increase can be slow, the camera 140 can capture images periodically during the temperature increase process. The controller 120 can record temperatures at which the camera 140 captures images.

The tuning instruction also cause the camera assembly 140 to captures images of the structured light pattern generated by the structured light projector 110 at each temperature in the set of temperatures. For example, the tuning instruction cause the camera assembly 140 to capture one or more images a pre-determined amount of time after the tuning instruction cause the wavelength regulator 115 to set the light source 113 to each temperature in the set of temperatures. The tuning instruction may further cause the camera assembly 140 to send the captured images to the controller 120.

In addition to generating the tuning instructions, the controller 120 also determines a temperature calibrated to the DOE 117 based on images captured by the camera assembly 140. The temperature calibrated to the DOE corresponds to a wavelength of light emitted by the light source 113 that results in at least one performance metric meeting a corresponding threshold value. For example, the temperature calibrated to the DOE 117 corresponds to the optimal wavelength for the DOE 117, i.e., a wavelength of emitted light that results in an estimated minimum power of a zeroth order diffracted beam of the structured light pattern. Note that the structured light pattern expands and contracts radially as wavelength of the light source 113 varies. In some embodiments, the optimal wavelength for the DOE 117 corresponds to optimal angular position of a higher order beam or minimum magnitude of pincushion distortion in the structured light pattern. Other examples of performance metric includes local uniformity, contrast, or other characteristics of the structured light pattern.

In some embodiments, the controller 120 determines a power of a zeroth order diffracted beam of the structured light pattern for at least some of the capture images. Each determined power value corresponds to a different temperature in the set of temperatures. For example, the controller 120 identifies a zeroth order diffracted beam in the captured images. In one embodiment, the zeroth order diffracted beam is the middle beam in a group of beams in each captured image. The controller 120 can also identify the zeroth order diffracted beam based on direction of the emitted light from the light source 113, as the zeroth order diffracted beam has the same direction as the emitted light. Further, the controller 120 determines a brightness of the zeroth order diffracted beam of the structured light pattern in one of the captured images. To determine the brightness value, the controller 120 may estimate digital counts in a captured image and transfer the estimated digital counts into the brightness value. In embodiments where the captured images are grayscale images, the controller 120 determines a lightness of the zeroth order diffracted beam of the structured light pattern. And the controller 120 determines a power of the zeroth order diffracted beam based on the determined brightness (or lightness) value. A higher brightness values corresponds to a higher power value. In embodiments where the camera assembly 140 captures multiple images at a temperature, the controller determine a power value for each of the multiple images and determines an average of the determined power values. The average power value is identified as the power value at the temperature.

In some embodiments, a power of a zeroth order diffracted beam can be measured by using a power meter (e.g., a calibrated thermopile, silicon detector, etc.). A mask can be installed in front of the DOE 117 to block higher order diffracted beams but allow the zeroth order diffracted beam to pass and enter into the power meter. For example, the mask is a plate including a hole in the direction of the zeroth order diffracted beam.

In some embodiments, the controller 120 determines a function describing power of the zeroth order diffracted beam as a function of temperature using each of the determined power values. Using the function, the controller 120 identifies a temperature that corresponds to a minimum power of the zeroth order diffracted beam. The identified temperature is the temperature calibrated to the DOE 117. For example, the controller 120 fits a curve that represents the function. The controller 120 identifies a point on the curve that corresponds to the minimum power value and determines the temperature value associated with the point. The temperature value associated with the point is the value of the temperature calibrated to the DOE 117. More details about fitting such a curve is described in conjunction with FIG. 2. As another example, the controller 120 determines an equation that represents the function. Using the equation, the controller 120 calculates the temperature value corresponding to a minimum power of the zeroth order diffracted beam. Accordingly, the temperature calibrated to the DOE 117 may not equal to any temperature value in the set of temperatures. The temperature calibrated to the DOE 117 can be stored in a database, an electrically erasable programmable read-only memory (EEPROM), etc. And the temperature calibrated to the DOE 117 can be retrieved to set the structured light projector 110 when the structured light projector 110 is installed in an end equipment, e.g., a HMD, a HMD console, or a HMD base-station.

In some other embodiment, the controller 120 ranks the different temperatures in accordance with their corresponding power of the zeroth order diffracted beam. From the ranked temperatures, the controller 120 select a temperature having a lowest power of power of the zeroth order diffracted beam. The selected temperature is the temperature calibrated to the DOE. Therefore, the temperature calibrated to the DOE 117 equals to a temperature value in the set of temperatures.

The controller 120 may determine a power of a zeroth order diffracted beam at each temperature in the set of temperatures. Alternatively, the controller 120 determines a power of zeroth order diffracted beam at each temperate in a subset of the set of temperatures. For example, the controller 120 obtains an estimated minimum power of zeroth ordered diffraction beam. The controller 120 determines a power of zeroth ordered diffraction beam for one temperature at a time and compares the determined power value with the estimated minimum power. If the determined power value is not larger than the minimum power, the controller 120 identifies the temperature corresponding to the determined power value as the temperature calibrated to the DOE 117. The controller 120 does not continue to determine a power of zeroth order diffracted beam for remaining temperatures. As another example, the controller 120 analyzes images captured by the camera assembly 140 in an order of increasing (or decreasing) temperature. The controller 120 compares a power of zeroth order diffracted beam at a temperature with a power of zeroth order diffracted beam at the next temperature in the order. The controller 120 can observe a trend from the comparison, e.g., the power of zeroth order diffracted beam increases with temperature. When the trend changes, the controller 120 identifies a minimum power of zeroth order diffracted beam and stops to analyze remaining captured images. The temperature calibrated to the DOE 117 may be provided to a user of the structured light projector 110 for further design of the structured light projector 110.

In some embodiment, the controller 120 determines a temperature that optimizes a particular performance metric in an iterative manner. For example, the controller 120 may initially use a relatively large increment to determine an initial set of temperatures. Based on this first set of temperature values, the controller 120 may determine that an optimal temperature value (i.e., the temperature value corresponding to the optimal wavelength value) is between two adjacent temperatures of the initial set of temperatures. The controller then sets a finer temperature interval (e.g., order of magnitude), and generates a second set of temperatures encompassed by the two adjacent values using the finer temperature interval. Based on this second set of temperature values, the controller 120 determines that an optimal temperature value is between two adjacent temperatures of the second set of temperatures. The controller 120 repeats this process until a value for the optimal temperature is determined that is within some accuracy threshold (e.g., within ±0.01° C.).

The tuning instructions generated by the controller 120 and information related to the determination of the temperature calibrated to the DOE 117 (including images captured by the camera assembly 140, the determined powers of zeroth order diffracted beams, the temperature calibrated to the DOE, etc.) can be stored in a database or in an EEPROM (not shown in FIG. 1) included in or otherwise associated with the structured light projector or the controller 120.

Figure 2:
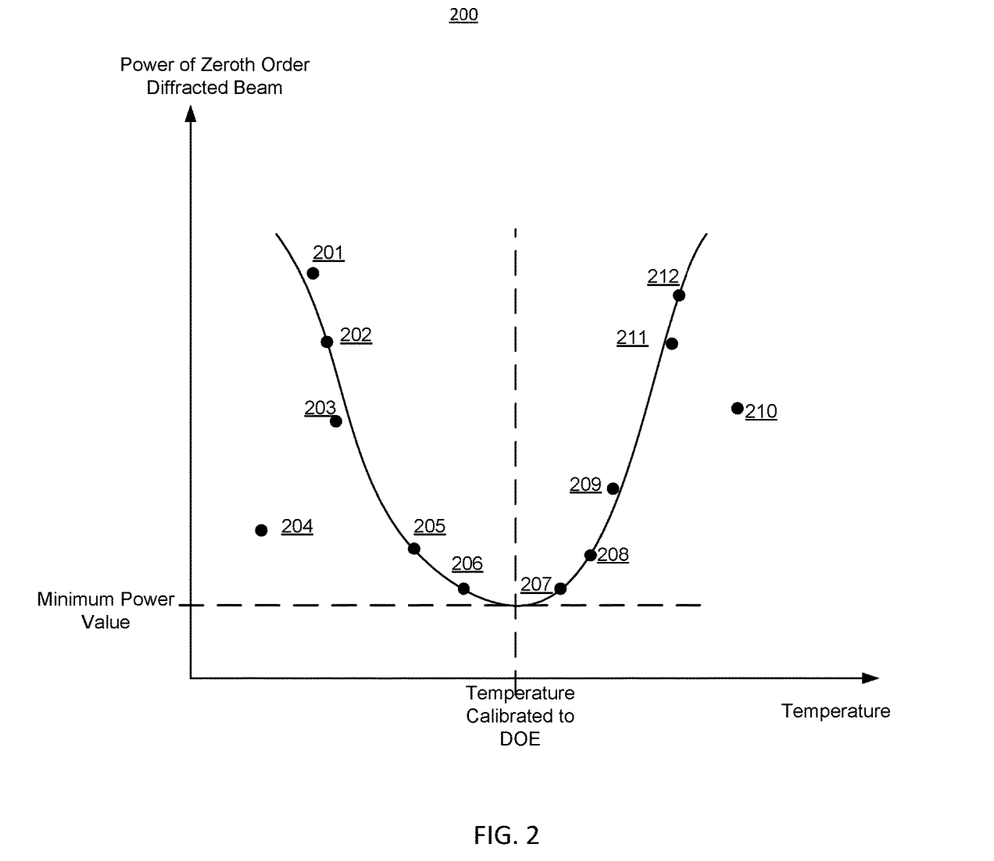
FIG. 2 is a curve illustrating power of zeroth order diffracted beam as a function of temperature, in accordance with an embodiment.

FIG. 2 is a curve 200 curve illustrating power of zeroth order diffracted beam as a function of temperature, in accordance with an embodiment. In one embodiment, the curve 200 is generated by a controller 120 of the wavelength tuning system 100. The horizontal axis in FIG. 2 represents temperature, and the vertical axis represents power of zeroth order diffracted beam. FIG. 2 includes 12 data points: 201-212. Each data point represents a different temperature value and a power of zeroth order diffracted beam at the temperature. Alternatively, there can be more or less data points.

The twelve data points are used to generate the curve 200 by the controller 120. As shown in FIG. 2, not all the twelve data points are on the curve 200. The data points 201, 203, 204, 209, 210, and 211 are off the curve 200. Particularly, the data points 204 and 210 are far off the curve 200. In one embodiment, the two data points 204 and 210 are not used to generate the curve 200, because the temperature or power values of the two data points 204 and 210 could have errors.

As shown by the curve 200, the power of zeroth order diffracted beam decreases with increasing temperature until it reaches a minimum power value. After the minimum power value, power value increases as temperature increases. The controller 120 identifies a temperature corresponding to the minimum power value. The identified temperature is the temperature calibrated to the DOE 117. In embodiments where the controller 120 selects a temperature from the set of temperatures as the temperature calibrated to the DOE 117, the controller 120 selects the temperature value of the data point 207 as the temperature calibrated to the DOE 117 because the data point 207 has the lowest power value of the twelve data points 201-212.

Figure 3:
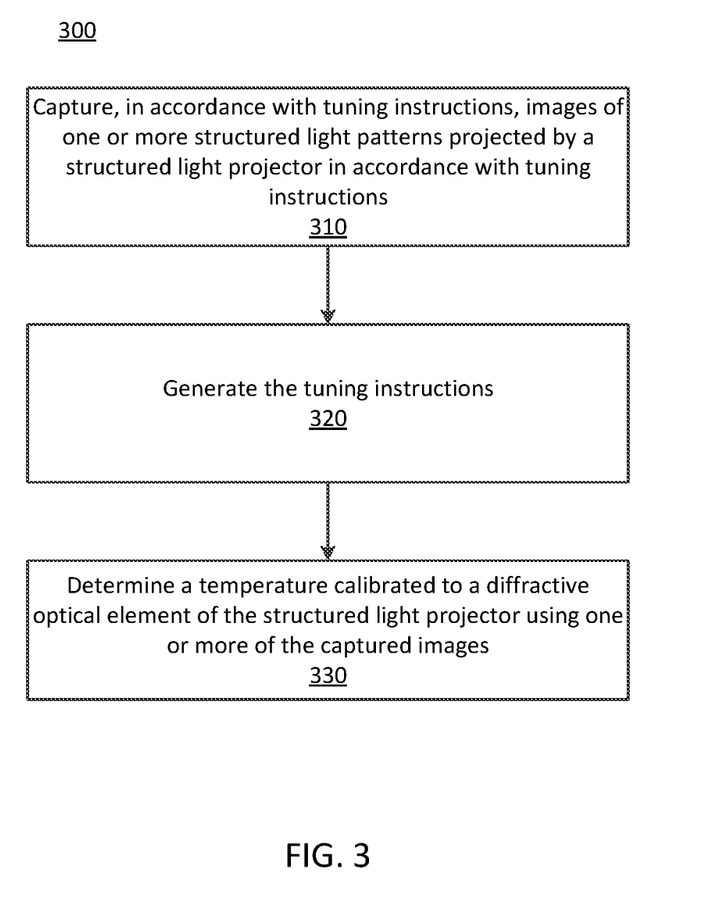
FIG. 3 is a flow chart illustrating a wavelength tuning process, in accordance with an embodiment.

FIG. 3 is a flow chart illustrating a wavelength tuning process, in accordance with an embodiment. In some embodiments, the process is performed by a wavelength tuning system 100. In alternative embodiments, the process can be performed by another system or device. Likewise, embodiments may include different and/or additional steps, or perform the steps in different orders.

The wavelength tuning system 100 captures 310, in accordance with tuning instructions, images of one or more structured light patterns projected by a structured light projector 110 in accordance with tuning instructions. In one embodiment, the images are captured by a camera assembly 140 of the wavelength tuning system 100. The captured images include images of structured light patterns captured at different temperature values of the laser light source 113. In some embodiments, the structured light patterns include diffuse light.

The wavelength tuning system 100 generates 320 the tuning instructions. In one embodiment, the tuning instructions are generated by a controller 120 of the wavelength tuning system 100. The tuning instructions cause a wavelength regulator 115 to set the laser light source 113 to different temperatures of one or more sets of temperatures as discussed in detail above with regard to FIG. 1. The tuning instructions also cause the camera assembly 140 to capture one or more images of the structured light pattern generated by the structured light projector 110 at each of the different temperatures.

The wavelength tuning system 100 determines 330 a temperature calibrated to the DOE 117 using one or more of the captured images. The temperature calibrated to the DOE 117 corresponds to a wavelength of light emitted by the laser light source that results in at least one performance metric meeting a corresponding threshold value. In one embodiment, the performance metric is power of zeroth order diffracted beam of the structured light pattern. And the corresponding threshold value is an estimated minimum power value. For example, using the captured images, the wavelength tuning system 100 determines brightness values of the zeroth order diffracted beam at some temperatures in the set of temperatures and determines power values based on the brightness values. Based on the determined power values, the wavelength tuning system 100 determines a minimum power value and identifies a temperature corresponding to the minimum power value. The identified temperature is the temperature calibrated to the DOE 117.

The temperature calibrated to the DOE 117 is used to configure the light source 113 so that the light source 110 emits light of wavelength optimal to the DOE 117. Accordingly, the DOE 117 has lowest diffraction efficiency for the zeroth order beam of the structured light pattern projected by the structured light projector 110, but increases power in one or more of the higher order diffracted beams. The increased power in the higher order beams is useful to increase intensity of a structured light pattern projected by the light source 113. Also, the higher order diffracted beams of the structured light pattern can be placed in their designed positions when the wavelength of the emitted light is optimal to the DOE 117.

Figure 4:
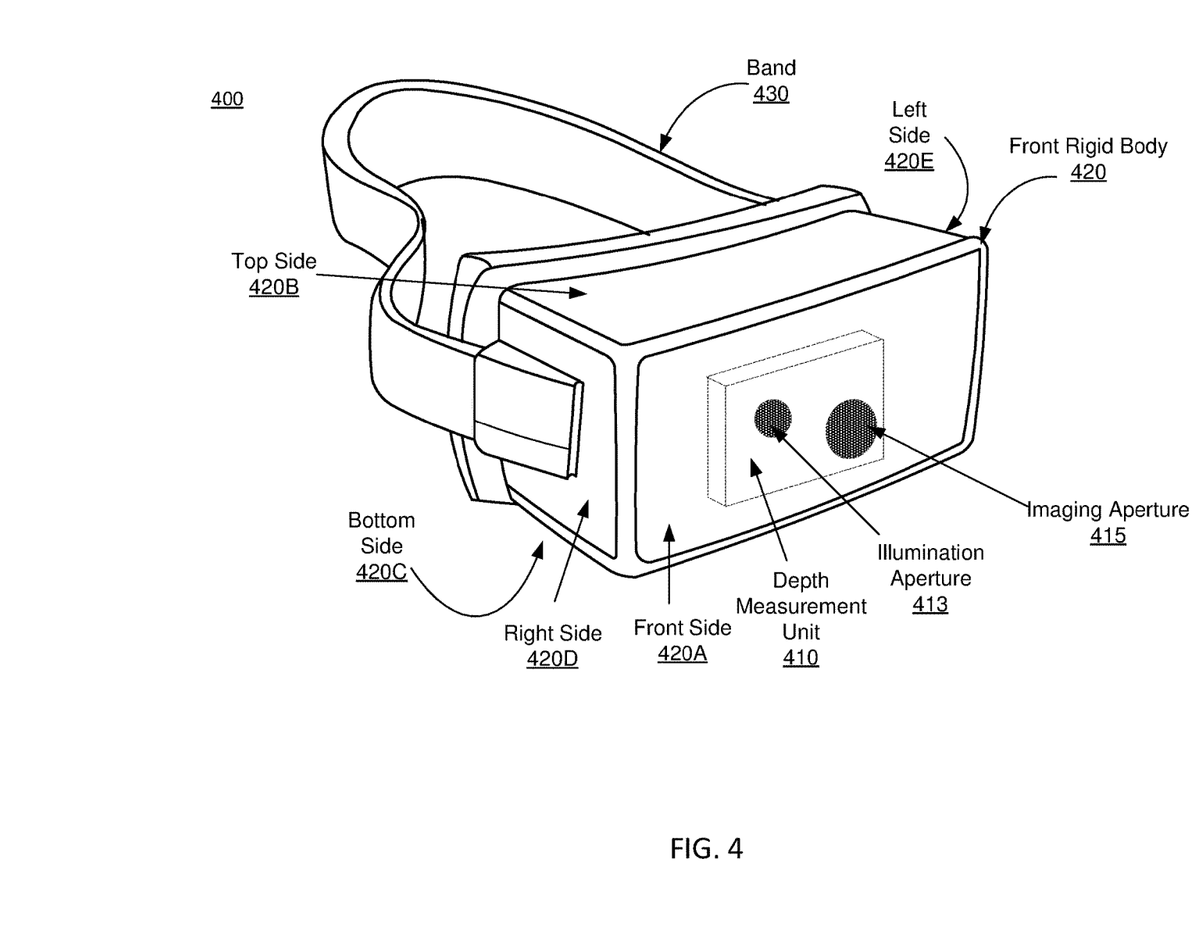
FIG. 4 is a wire diagram of a HMD including a depth measurement unit, in accordance with an embodiment.

FIG. 4 is a wire diagram of a HMD including a depth measurement unit 430, in accordance with an embodiment. The HMD 400 is a head-mounted display that presents media to a user comprising virtual and/or augmented views of a physical, real-world environment with computer-generated elements. Examples of the media presented by the HMD 400 include images (e.g., 2D or 3D images), video (e.g., 2D or 3D video), audio, or some combination thereof. Images and video can be presented to each of the eyes of the user by using electronic displays and optical lenses (shown in FIG. 2) of the HMD 400.

The HMD 400 may be part of, e.g., a virtual reality (VR) system, an augmented reality (AR) system, a (mixed reality) MR system, or some combination thereof. In embodiments that describe AR system and/or a MR system, portions of the HMD 400 that are between a front side (or some other side) of the HMD 400 and an eye of the user are at least partially transparent (e.g., a partially transparent electronic display). In embodiments that describe AR system and/or a MR system, portions of the HMD 400 that are between a front side of the HMD 400 and an eye of the user are at least partially transparent (e.g., a partially transparent electronic display).

The depth measurement unit 410 determines depth information for one or more objects in a local area. The local area may be an area where the user's eye is located, e.g., an eye box of the HMD 400 (not shown in FIG. 4). Alternatively, the local area can be an area surrounding the HMD 400. The depth measurement unit 410 comprises a structured light projector and a depth camera (both not shown in FIG. 4). The depth camera captures images of an object (e.g., an eye of a user) illuminated with a structured light pattern projected by the structured light projector.

The structured light projector can be the structured light projector 110. For example, the structured light projector includes a light source 113 configured to calibrated to a DOE 117 of the structured light projector, i.e., the light source 113 is configured to operate at a temperature calibrated to the DOE 117 and emit light with a wavelength optimal to the DOE 117. The depth camera can be a camera of the camera assembly 140 or a different type of camera. For example, the depth camera can be an augmented camera described in U.S. Patent Appl. No. 62/452,167, which is incorporated by reference herein. The depth measurement unit 410 is incorporated into the HMD 400 and is not visible to a user of the HMD 400. The HMD 400 shown in FIG. 4 depicts an illumination aperture 413 and an imaging aperture 415. The structured light projector projects structured light through the illumination aperture 413. And the depth camera captures structured light reflected from an object in a local area through the image aperture 415. The depth measurement unit 410 also includes a controller that coordinates how the structured light projector projects structured light and how the depth camera captures images, and determines depth information for objects in images captured by the depth camera using portions of the structured light pattern in the captured images.

As the structured light projector is configured to operate at a temperature calibrated to the DOE 117, it is tuned to produce minimum power in the zeroth order diffracted beam of the structured light pattern, thus, increasing power in higher order diffracted beams. Such tuning increases the intensity of the structured light pattern making it easier for the depth measurement unit to distinguish the structured light pattern in images captured by the depth camera. Moreover, such tuning mitigates risk of non-compliance with eye safety standards that dictate what constitutes safe levels of exposure to, e.g., laser light. Additionally, a structured light pattern can grow or shrink radially if wavelength of the light source is mismatched to the optimal wavelength of the DOE 117. Mismatched wavelengths can also cause lower transmission of the light through the DOE 117 and coatings, if any.

Additional Configuration Information

The foregoing description of the embodiments of the disclosure has been presented for the purpose of illustration; it is not intended to be exhaustive or to limit the disclosure to the precise forms disclosed. Persons skilled in the relevant art can appreciate that many modifications and variations are possible in light of the above disclosure.

Some portions of this description describe the embodiments of the disclosure in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments of the disclosure may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments of the disclosure may also relate to a product that is produced by a computing process described herein. Such a product may comprise information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the disclosure be limited not by this detailed description, but rather by any claims that issue on an application based hereon. Accordingly, the disclosure of the embodiments is intended to be illustrative, but not limiting, of the scope of the disclosure, which is set forth in the following claims.

What is claimed is:

1. A wavelength tuning system comprising:
a camera configured to capture, in accordance with tuning instructions, images of one or more structured light patterns projected by a structured light projector in accordance with the tuning instructions, the structured light projector comprising a laser light source, a wavelength regulator that regulates temperature of the laser light source, and a diffractive optical element (DOE) that generates structured light patterns using light from the laser light source, and the captured images include images of structured light patterns captured at different temperature values of the light laser source; and
a controller configured to:
generate the tuning instructions that cause the wavelength regulator to set the laser light source to different temperatures of a set of temperatures, and the camera to capture images of the structured light pattern generated by the structured light projector at each of the different temperatures, and
determine a temperature calibrated to the DOE using one or more of the captured images, wherein the temperature calibrated to the DOE corresponds to a wavelength of light emitted by the laser light source that results in an estimated minimum power of a zeroth order diffracted beam of the structured light pattern.

2. The system of claim 1, wherein the controller is further configured to:
determine a power of a zeroth order diffracted beam of the structured light pattern for some of the captured images, wherein each determined power value corresponds to a different temperature in the set of temperatures.

3. The system of claim 2, wherein the controller is further configured to:
determine a function describing power of the zeroth order diffracted beam as a function of temperature using each of the determined power values; and
identify a temperature that corresponds to a minimum power of the zeroth order diffracted beam using the function, wherein the identified temperature is the temperature calibrated to the DOE.

4. The system of claim 2, the controller is further configured to:
determine a brightness of a zeroth order diffracted beam of the structured light pattern in one of the captured images; and
determine a power of the zeroth order diffracted beam based on the determined brightness value.

5. The system of claim 1, wherein the controller is further configured to:
determine a power of a zeroth order diffracted beam of the structured light pattern for some of the captured images, wherein each determined power value corresponds to a different temperature in the set of temperatures;
rank the different temperatures in accordance with their corresponding power of the zeroth order diffracted beam; and
select a temperature from the ranked temperatures as the temperature calibrated to the DOE, the selected temperature having a lowest power of power of the zeroth order diffracted beam.

6. The system of claim 1, wherein the wavelength regulator is a thermal electric cooler that is coupled directly to the laser light source, and the thermal electric cooler regulates a temperature of the laser light source in accordance with the tuning instructions.

7. The system of claim 1, wherein the wavelength regulator is a resistive heater that is coupled directly to the laser light source, and the resistive heater regulates a temperature of the laser light source in accordance with the tuning instructions.

8. The system of claim 1, wherein the controller is further configured to:
determine a range of temperatures in the set of temperatures, wherein an increment between a temperature adjacent to a predicted temperature value for the temperature calibrated to the DOE is smaller than an increment between a temperature adjacent to a maximum temperature in the set of temperatures.

9. The system of claim 1, wherein the controller is further configured to:
determine a range of temperatures in the set of temperatures, wherein an increment between adjacent temperature values in the set of temperature values is constant.

10. A method comprising:
capturing, in accordance with tuning instructions, images of one or more structured light patterns projected by a structured light projector in accordance with the tuning instructions, the structured light projector comprising a laser light source, a wavelength regulator that regulates temperature of the laser light source, and a diffractive optical element (DOE) that generates structured light patterns using light from the laser light source, and the captured images include images of structured light patterns captured at different temperature values of the light laser source;

generating the tuning instructions that cause the wavelength regulator to set the laser light source to different temperatures of a set of temperatures, and the camera to capture images of the structured light pattern generated by the structured light projector at each of the different temperatures; and determining a temperature calibrated to the DOE using one or more of the captured images, wherein the temperature calibrated to the DOE corresponds to a wavelength of light emitted by the laser light source that results in an estimated minimum power of a zeroth order diffracted beam of the structured light pattern.

11. The method of claim 10, wherein determining the temperature calibrated to the DOE using one or more of the captured images comprises:

determining a power of a zeroth order diffracted beam of the structured light pattern for some of the captured images, wherein each determined power value corresponds to a different temperature in the set of temperatures.

12. The method of claim 11, wherein determining the temperature calibrated to the DOE using one or more of the captured images, further comprises:

determining, using each of the determined power values, a function describing power of the zeroth order diffracted beam as a function of temperature; and identifying a temperature that correspond to a minimum power of the zeroth order diffracted beam using the function, wherein the identified temperature is the temperature calibrated to the DOE.

13. The method of claim 11, wherein determining the temperature calibrated to the DOE using one or more of the captured images, further comprises:

determining a brightness of a zeroth order diffracted beam of the structured light pattern in one of the captured images; and determining a power of the zeroth order diffracted beam based on the determined brightness value.

14. The method of claim 10, wherein determining the temperature calibrated to the DOE using one or more of the captured images, further comprises:

determining a power of a zeroth order diffracted beam of the structured light pattern for some of the captured images, wherein each determined power value corresponds to a different temperature in the set of temperatures;

ranking the different temperatures in accordance with their corresponding power of the zeroth order diffracted beam; and selecting a temperature from the ranked temperatures as the temperature calibrated to the DOE, the selected temperature having a lowest power of power of the zeroth order diffracted beam.

15. The method of claim 10, wherein generating the tuning instructions that cause the wavelength regulator to set the laser light source to different temperatures of a set of temperatures, and the camera to capture images of the structured light pattern generated by the structured light projector at each of the different temperatures comprises:

determining a range of temperatures in the set of temperatures, wherein an increment between a temperature adjacent to a predicted temperature value for the temperature calibrated to the DOE is smaller than an increment between a temperature adjacent to a maximum temperature in the set of temperatures.

16. The method of claim 10, wherein generating the tuning instructions that cause the wavelength regulator to set the laser light source to different temperatures of a set of temperatures, and the camera to capture images of the structured light pattern generated by the structured light projector at each of the different temperatures comprises:

determining a range of temperatures in the set of temperatures, wherein an increment between adjacent temperature values in the set of temperature values is constant.

17. A wavelength tuning system comprising:

a camera configured to capture, in accordance with tuning instructions, images of one or more structured light patterns projected by a structured light projector in accordance with the tuning instructions, the structured light projector comprising a laser light source, a wavelength regulator that regulates temperature of the laser light source, and a diffractive optical element (DOE) that generates structured light patterns using light from the laser light source, and the captured images include images of structured light patterns captured at different temperature values of the light laser source; and a controller configured to:

generate the tuning instructions that cause the wavelength regulator to set the laser light source to different temperatures of a set of temperatures, and the camera to capture images of the structured light pattern generated by the structured light projector at each of the different temperatures, determine a temperature calibrated to the DOE using one or more of the captured images, wherein the temperature calibrated to the DOE corresponds to a wavelength of light emitted by the laser light source that results in at least one performance metric meeting a corresponding threshold value.

18. The system of claim 17, wherein the wavelength regulator is a thermal electric cooler that is coupled directly to the laser light source, and the thermal electric cooler regulates a temperature of the laser light source in accordance with the tuning instructions.

19. The system of claim 17, wherein the wavelength regulator is a resistive heater that is coupled directly to the laser light source, and the resistive heater regulates a temperature of the laser light source in accordance with the tuning instructions.

20. The system of claim 17, wherein the controller is further configured to:

determine a range of temperatures in the set of temperatures, wherein an increment between a temperature adjacent to a predicted temperature value for the temperature calibrated to the DOE is smaller than an increment between a temperature adjacent to a maximum temperature in the set of temperatures.

* * * * *